(12) United States Patent
Northcutt et al.

(10) Patent No.: US 10,143,501 B2
(45) Date of Patent: *Dec. 4, 2018

(54) EXPANDABLE INTERSPINOUS DEVICE

(71) Applicant: Phygen, LLC, Irvine, CA (US)

(72) Inventors: Trent Northcutt, Oceanside, CA (US); Laszlo Garamszegi, Mission Viejo, CA (US); Bryan Okamoto, Irvine, CA (US)

(73) Assignee: Aurora Spine, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/151,336

(22) Filed: May 10, 2016

(65) Prior Publication Data

US 2016/0249961 A1    Sep. 1, 2016

Related U.S. Application Data

(63) Continuation of application No. 13/761,031, filed on Feb. 6, 2013, now Pat. No. 9,387,016, which is a continuation of application No. 13/526,277, filed on Jun. 18, 2012, now abandoned.

(60) Provisional application No. 61/515,541, filed on Aug. 5, 2011, provisional application No. 61/498,354, filed on Jun. 17, 2011.

(51) Int. Cl.
*A61B 17/70* (2006.01)
*A61B 17/68* (2006.01)

(52) U.S. Cl.
CPC ...... *A61B 17/7068* (2013.01); *A61B 17/7065* (2013.01); *A61B 2017/681* (2013.01)

(58) Field of Classification Search
CPC ............ A61B 17/7047; A61B 17/7071; A61B 17/7067; A61B 17/7068; A61B 17/7065; A61B 2017/0256
See application file for complete search history.

(56) References Cited

U.S. PATENT DOCUMENTS

| | | |
|---|---|---|
| 5,011,484 A | 4/1991 | Breard |
| 5,496,318 A | 3/1996 | Howland et al. |
| 5,645,599 A | 7/1997 | Samani |
| 5,876,404 A | 3/1999 | Zucherman et al. |
| 6,099,527 A | 8/2000 | Hochschuler et al. |
| 6,238,397 B1 | 5/2001 | Zucherman et al. |
| 6,312,431 B1 | 11/2001 | Asfora |
| 6,451,020 B1 | 9/2002 | Zucherman et al. |
| 6,585,739 B2 | 7/2003 | Kuras et al. |

(Continued)

OTHER PUBLICATIONS

Cylinder, definition from Dictionary.com, 1 page, printed Jan. 21, 2015.

*Primary Examiner* — Lynnsy Summitt
(74) *Attorney, Agent, or Firm* — Hybrid Law Group PC

(57) ABSTRACT

Disclosed is a device that is configured to be implanted adjacent interspinous processes of a patient. In one aspect, a spinal implant device comprises: a spacer region adapted to be positioned between first and second spinous processes of first and second vertebral bodies to limit movement of the first spinous process and the second spinous process toward one another; and an attachment region attached to the spacer region, the attachment region adapted to attach to the first spinous process via a fastener, the attachment region comprising a pair of pads having attachment elements that are configured to attach onto the spinous process.

7 Claims, 13 Drawing Sheets

(56) References Cited

U.S. PATENT DOCUMENTS

| | | |
|---|---|---|
| 6,626,944 B1 | 9/2003 | Taylor |
| 6,695,842 B2 | 2/2004 | Zucherman et al. |
| 6,761,720 B1 | 7/2004 | Senegas |
| 6,946,000 B2 | 9/2005 | Senegas et al. |
| 7,048,736 B2 | 5/2006 | Robinson et al. |
| 7,087,083 B2 | 8/2006 | Pasquet et al. |
| 7,238,204 B2 | 7/2007 | Le et al. |
| 7,442,208 B2 | 10/2008 | Mathieu et al. |
| 7,510,567 B2 | 3/2009 | Zucherman et al. |
| 7,520,888 B2 | 4/2009 | Trieu |
| 7,585,313 B2 | 9/2009 | Kwak et al. |
| 7,585,316 B2 | 9/2009 | Trieu |
| 7,682,376 B2 | 3/2010 | Trieu |
| 7,691,130 B2 | 4/2010 | Bruneau et al. |
| 7,727,233 B2 | 6/2010 | Blackwell et al. |
| 7,763,073 B2 | 7/2010 | Hawkins et al. |
| 7,776,069 B2 | 8/2010 | Taylor |
| 7,837,688 B2 | 11/2010 | Boyer, II et al. |
| 7,871,426 B2 | 1/2011 | Chin et al. |
| 7,879,073 B2 | 2/2011 | Pasquet et al. |
| 7,879,104 B2 | 2/2011 | Dewey et al. |
| 7,922,750 B2 | 4/2011 | Trautwein et al. |
| 8,048,077 B2 | 11/2011 | Morales et al. |
| 8,048,120 B1 | 11/2011 | Fallin et al. |
| 8,070,779 B2 | 12/2011 | Khoo |
| 8,100,945 B2 | 1/2012 | Dewey et al. |
| 8,114,132 B2 | 2/2012 | Lyons et al. |
| 8,114,136 B2 | 2/2012 | Carls et al. |
| 8,118,839 B2 | 2/2012 | Taylor |
| 8,128,659 B2 | 3/2012 | Ginsberg et al. |
| 8,133,227 B2 | 3/2012 | Morales et al. |
| 8,157,842 B2 | 4/2012 | Phan et al. |
| 8,167,915 B2 | 5/2012 | Ferree et al. |
| 8,187,306 B2 | 5/2012 | Fallin et al. |
| 8,192,465 B2 | 6/2012 | Fallin et al. |
| 8,206,420 B2 | 6/2012 | Patel et al. |
| 8,216,276 B2 | 7/2012 | Trieu |
| 8,216,279 B2 | 7/2012 | Bruneau et al. |
| 8,221,462 B2 | 7/2012 | Dwyer et al. |
| 8,221,464 B2 | 7/2012 | Belliard et al. |
| 8,226,653 B2 | 7/2012 | Blackwell et al. |
| 8,236,031 B2 | 8/2012 | Bucci |
| 8,241,330 B2 | 8/2012 | Lamborne et al. |
| 8,241,332 B2 | 8/2012 | Ciupik et al. |
| 8,246,655 B2 | 8/2012 | Jackson et al. |
| 8,308,769 B2 | 11/2012 | Farr |
| 8,313,513 B2 | 11/2012 | Beger et al. |
| 8,343,190 B1 | 1/2013 | Mueller et al. |
| 8,349,016 B2 | 1/2013 | Le et al. |
| 8,357,181 B2 | 1/2013 | Lange et al. |
| 8,372,117 B2 | 2/2013 | Phan et al. |
| 8,372,118 B2 | 2/2013 | Chin et al. |
| 8,377,097 B2 | 2/2013 | Gordon et al. |
| 8,382,801 B2 | 2/2013 | Lamborne et al. |
| 8,388,656 B2 | 3/2013 | Sheffer et al. |
| 8,388,657 B2 | 3/2013 | Boyer, II et al. |
| 8,403,959 B2 | 3/2013 | Doellinger |
| 8,414,615 B2 | 4/2013 | Weng et al. |
| 8,419,738 B2 | 4/2013 | Smisson, III et al. |
| 8,425,560 B2 | 4/2013 | Massoudi |
| 8,430,911 B2 | 4/2013 | Chin et al. |
| 9,387,016 B2 | 7/2016 | Okamoto et al. |
| 2005/0075634 A1 | 4/2005 | Zucherman et al. |
| 2005/0203512 A1 | 9/2005 | Hawkins et al. |
| 2006/0015181 A1 | 1/2006 | Elberg |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0247623 A1 | 11/2006 | Anderson et al. |
| 2006/0247634 A1 | 11/2006 | Warner et al. |
| 2006/0247640 A1 | 11/2006 | Blackwell et al. |
| 2006/0271044 A1 | 11/2006 | Petrini et al. |
| 2007/0093823 A1 | 4/2007 | Booth et al. |
| 2007/0093830 A1 | 4/2007 | Zucherman et al. |
| 2007/0106298 A1 | 5/2007 | Carli et al. |
| 2007/0162001 A1 | 7/2007 | Chin et al. |
| 2007/0162004 A1 | 7/2007 | Tornier et al. |
| 2007/0167945 A1 | 7/2007 | Lange et al. |
| 2007/0179500 A1 | 8/2007 | Chin et al. |
| 2007/0203494 A1 | 8/2007 | Arnin et al. |
| 2007/0213829 A1 | 9/2007 | Le et al. |
| 2008/0114455 A1 | 5/2008 | Lange et al. |
| 2008/0140125 A1 | 6/2008 | Mitchell et al. |
| 2008/0161856 A1 | 7/2008 | Liu et al. |
| 2008/0167657 A1 | 7/2008 | Greenhalgh |
| 2008/0183218 A1* | 7/2008 | Mueller ............ A61B 17/7068 606/280 |
| 2008/0275511 A1 | 11/2008 | Weinacker et al. |
| 2008/0294199 A1 | 11/2008 | Kohm et al. |
| 2008/0294200 A1 | 11/2008 | Kohm et al. |
| 2009/0138087 A1 | 5/2009 | Miglietta et al. |
| 2009/0264927 A1* | 10/2009 | Ginsberg ........... A61B 17/7068 606/246 |
| 2009/0270918 A1 | 10/2009 | Attia et al. |
| 2009/0270919 A1 | 10/2009 | Dos Reis, Jr. |
| 2009/0318967 A1 | 12/2009 | Jeon et al. |
| 2010/0010548 A1 | 1/2010 | Hermida |
| 2010/0069965 A1 | 3/2010 | Abdou |
| 2010/0087869 A1 | 4/2010 | Abdou |
| 2010/0121379 A1 | 5/2010 | Edmond |
| 2010/0204732 A1 | 8/2010 | Aschmann et al. |
| 2010/0217320 A1 | 8/2010 | Landis |
| 2010/0241167 A1 | 9/2010 | Taber et al. |
| 2010/0305619 A1 | 12/2010 | Knoepfle et al. |
| 2011/0004248 A1 | 1/2011 | Abdou |
| 2011/0022090 A1* | 1/2011 | Gordon ............. A61B 17/7068 606/249 |
| 2011/0040330 A1 | 2/2011 | Sheffer |
| 2011/0066186 A1 | 3/2011 | Boyer, II et al. |
| 2011/0087285 A1 | 4/2011 | Khajavi et al. |
| 2011/0098745 A1 | 4/2011 | Liu et al. |
| 2011/0144692 A1 | 6/2011 | Saladin et al. |
| 2011/0313458 A1 | 12/2011 | Butler et al. |
| 2011/0319936 A1 | 12/2011 | Gordon et al. |
| 2012/0010660 A1 | 1/2012 | Fallin et al. |
| 2012/0016418 A1 | 1/2012 | Chin et al. |
| 2012/0065683 A1 | 3/2012 | Kuo et al. |
| 2012/0083844 A1 | 4/2012 | Linares |
| 2012/0089184 A1 | 4/2012 | Yeh |
| 2012/0101528 A1 | 4/2012 | Souza et al. |
| 2012/0109198 A1 | 5/2012 | Dryer et al. |
| 2012/0109203 A1 | 5/2012 | Dryer et al. |
| 2012/0109204 A1 | 5/2012 | Linares |
| 2012/0136390 A1 | 5/2012 | Butler et al. |
| 2012/0143252 A1 | 6/2012 | Robinson |
| 2012/0150228 A1 | 6/2012 | Zappacosta et al. |
| 2012/0191135 A1 | 7/2012 | Abdou |
| 2012/0221051 A1 | 8/2012 | Robinson |
| 2012/0290008 A1 | 11/2012 | Kirschman |
| 2012/0296278 A1 | 11/2012 | Schraga |
| 2012/0296377 A1 | 11/2012 | Ferree et al. |
| 2013/0012995 A1 | 1/2013 | Butterfield et al. |
| 2013/0012996 A1 | 1/2013 | Zamani et al. |
| 2013/0041408 A1 | 2/2013 | Dinville et al. |
| 2013/0060285 A1 | 3/2013 | Bucci et al. |
| 2013/0072979 A1 | 3/2013 | Butler et al. |
| 2013/0090689 A1 | 4/2013 | Villavicencio |
| 2013/0103088 A1 | 4/2013 | Karahalios et al. |
| 2013/0103089 A1 | 4/2013 | Gordon et al. |
| 2013/0184752 A1 | 7/2013 | Binder |
| 2013/0296940 A1 | 11/2013 | Northcutt et al. |

* cited by examiner

EXPANDABLE INTERSPINOUS DEVICE

REFERENCE TO PRIORITY DOCUMENTS

This application is a continuation of U.S. patent application Ser. No. 13/761,031, filed Feb. 6, 2013, which is a continuation of U.S. patent application Ser. No. 13/526,277, filed Jun. 18, 2012, which claims priority of co-pending U.S. Provisional Patent Application Ser. No. 61/515,541 entitled EXPANDABLE INTERSPINOUS DEVICE and filed on Aug. 5, 2011, and co-pending U.S. Provisional Patent Application Ser. No. 61/498,354 entitled EXPANDABLE INTERSPINOUS DEVICE and filed on Jun. 17, 2011. The disclosures of the Provisional Patent Applications are hereby incorporated by reference in their entirety.

BACKGROUND

Many people suffers from back pain due to any of a variety of factors. Such back pain can sometime be treated by introducing interspinous implants between the spinous processes of adjacent vertebral bodies in a patient's spine. This can maintain the stability of the vertebral column to increase the size of the spinal canal and allow the patient to have normal mobility.

There currently is need for improved device that can be implanted between spinous processes.

SUMMARY

Disclosed is a device that is configured to be implanted adjacent interspinous processes of a patient. In one aspect, a spinal implant device comprises: a spacer region adapted to be positioned between first and second spinous processes of first and second vertebral bodies to limit movement of the first spinous process and the second spinous process toward one another; and an attachment region attached to the spacer region, the attachment region adapted to attach to the first spinous process via a fastener, the attachment region comprising a pair of pads having attachment elements that are configured to attach onto the spinous process.

Other features and advantages should be apparent from the following description of various embodiments, which illustrate, by way of example, the principles of the invention.

BRIEF DESCRIPTION OF THE DRAWINGS

FIGS. 6-10A show another embodiment of an interspinous device.

FIGS. 10B-11 show another embodiment of an interspinous device.

DETAILED DESCRIPTION

Before the present subject matter is further described, it is to be understood that this subject matter described herein is not limited to particular embodiments described, as such may of course vary. It is also to be understood that the terminology used herein is for the purpose of describing particular embodiments only, and is not intended to be limiting. Unless defined otherwise, all technical terms used herein have the same meaning as commonly understood by one skilled in the art to which this subject matter belongs.

As will be apparent to those of skill in the art upon reading this disclosure, each of the individual embodiments described and illustrated herein has discrete components and features which may be readily separated from or combined with the features of any of the other several embodiments without departing from the scope of the subject matter described herein. Any recited method can be carried out in the order of events recited or in any other order which is logically possible.

Figure 1:
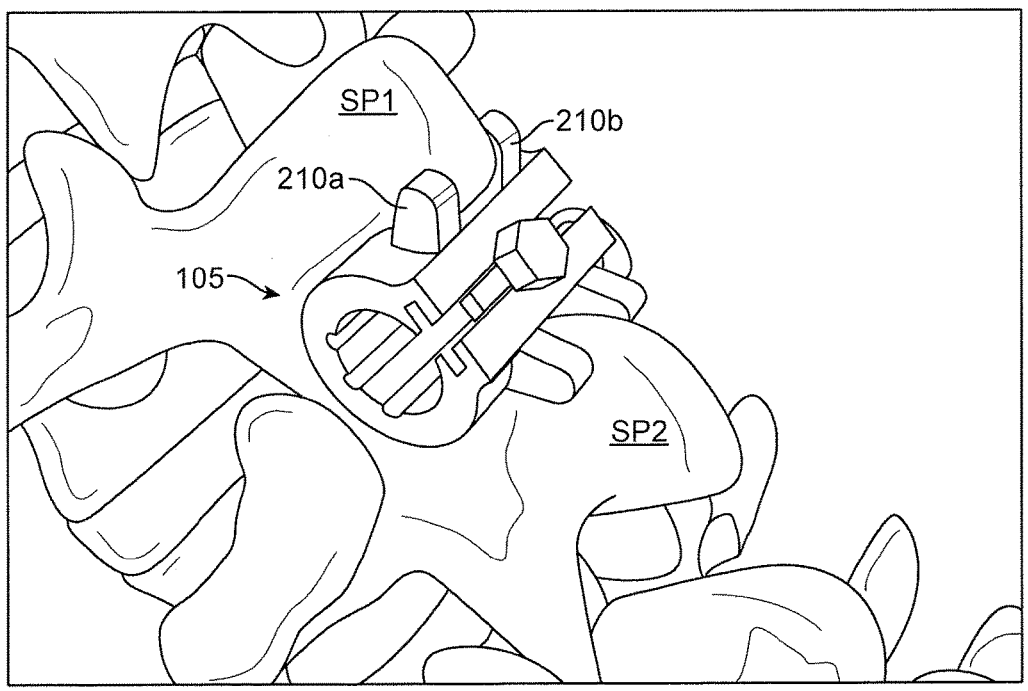
FIG. 1 shows a perspective view of a device that is configured for placement between the spinous processes of two adjacent vertebral bodies.
Figure 2:
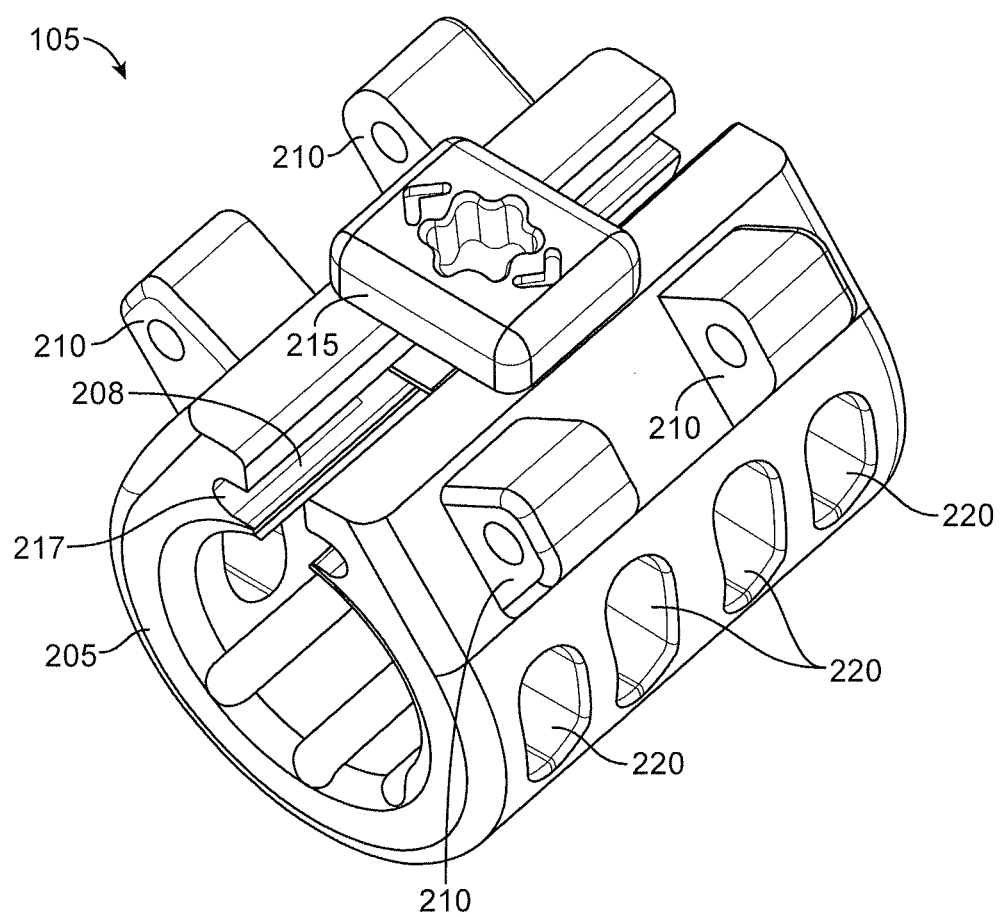
FIG. 2 shows an enlarged, perspective view of the device of FIG. 1.
Figure 3:
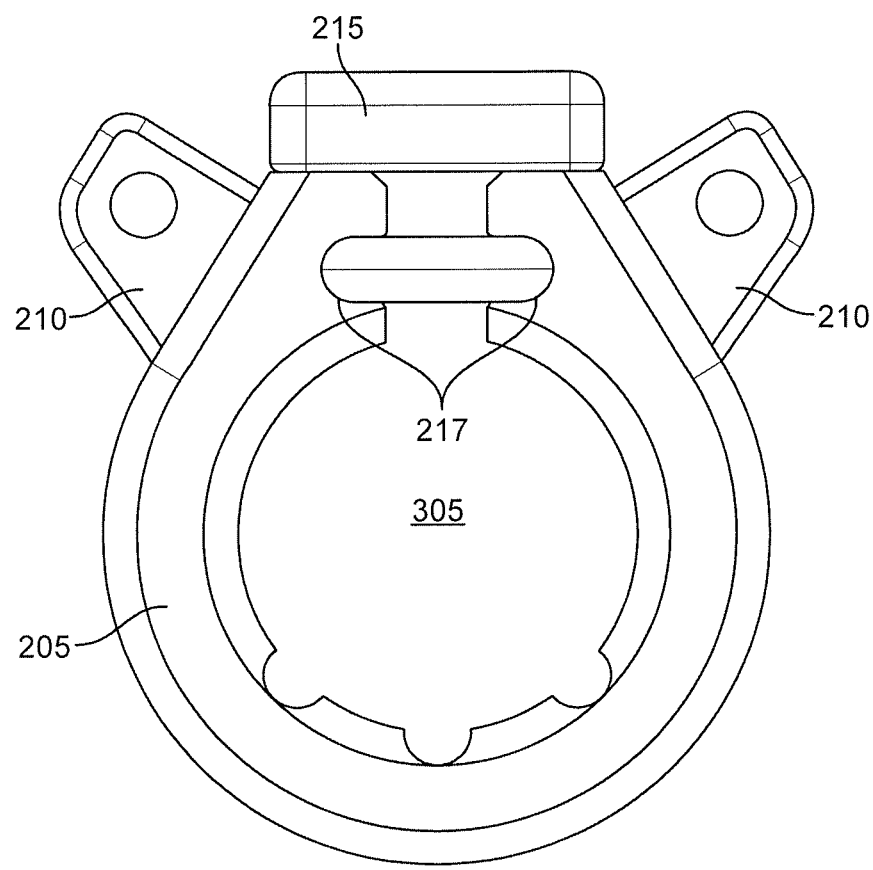
FIG. 3 shows a side view of the device of FIG. 1.

FIG. 1 shows a perspective view of a device 105 that is configured for placement between the spinous processes SP1 and SP2 of two adjacent vertebral bodies. FIG. 2 shows an enlarged, perspective view of the device 105 and FIG. 3 shows a side view of the device 105. The device 105 includes a spacer or central region 205 that is sized and shaped to fit between the spinous processes of the two adjacent vertebral bodies. The device 105 further includes a pair of protrusions 210 that extend outward from the central region. The protrusions are size and shaped to couple to the spinous processes, as described more fully below.

With reference to FIGS. 2 and 3, the central region 205 comprises a cylindrical body having one or more openings that extend through the walls of the body. In the illustrated embodiment, the central region 205 is cylindrical and substantially circular when viewed from the side (as shown in FIG. 3). A central shaft 305 extends through the central region 205. Along an upper portion of the central region 205, an elongated gap 208 is formed, which is sized and shaped to receive a locking member 215, as described below. It should be appreciated that the central region 205 can have other shapes.

With reference still to FIGS. 2 and 3, the protrusions 210 comprise outwardly extending bodies or tabs. A pair of such protrusions extends outwardly from the central region 205 on each side of the gap 208. A space between each of the protrusions is sized and shaped to receive at least a portion of a spinous process. For example, as shown in FIG. 1, the protrusions 210a and 210b define a space therebetween that is sized and shaped to receive the spinous process SP1. In this manner, the device 105 can be positioned between the spinous processes SP1 and SP2 with the protrusions 210 coupling to respective spinous processes to thereby serve anchoring or stabilizing functions.

As shown in FIGS. 2 and 3, the locking member 215 is sized and shaped to fit within the elongated gap 215. In this regard, as shown in FIG. 3, the elongated gap 215 forms a pair of slots that are sized and shaped to receive complementary-shaped tabs on the locking member 215. This permits the locking member 215 to be slidably positioned into the gap 215 by properly aligning the locking member adjacent the gap 215 and then sliding the locking member into the gap along a vector that would be normal to the plane of FIG. 3. After the locking member is positioned in the gap 215, locking member may be rotated to cause a cam portion of the locking member to outwardly separate the central region along opposite sides of the gap 215 and thereby lock the central region onto the spinous processes.

Figure 4:
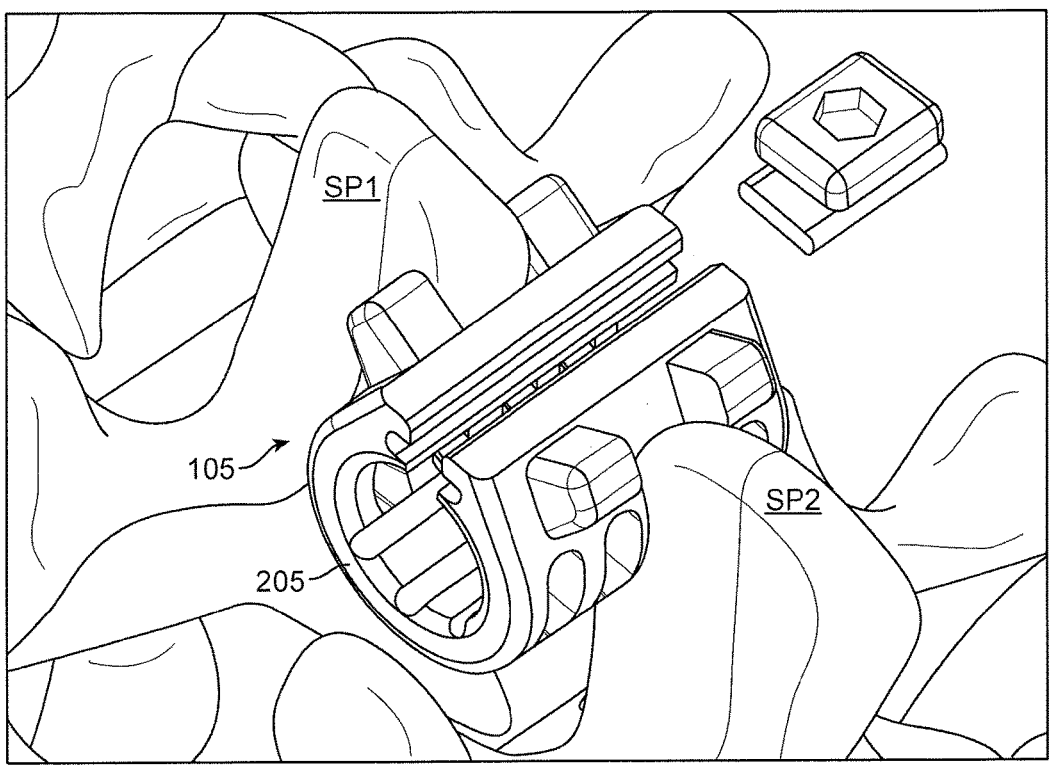
FIG. 4 shows the device positioned between a pair of spinous processes.

This is described in more detail with reference to FIG. 4, which shows the central region 205 of the device 105 positioned between a pair of spinous processes SP1 and SP2.

At this stage, the locking member 215 is not coupled to the central region 205. The locking member 215 can now be slid into the central region and rotated to cause the cam to expand the central region such that it exerts a force onto the spinous processes and fixes thereto. Note that a series of slots 220 (FIG. 2) are located along the wall of the central region 205. The slots are sized and shaped to receive at least a portion of a spinous process when the device 105 is implanted.

Figure 5:
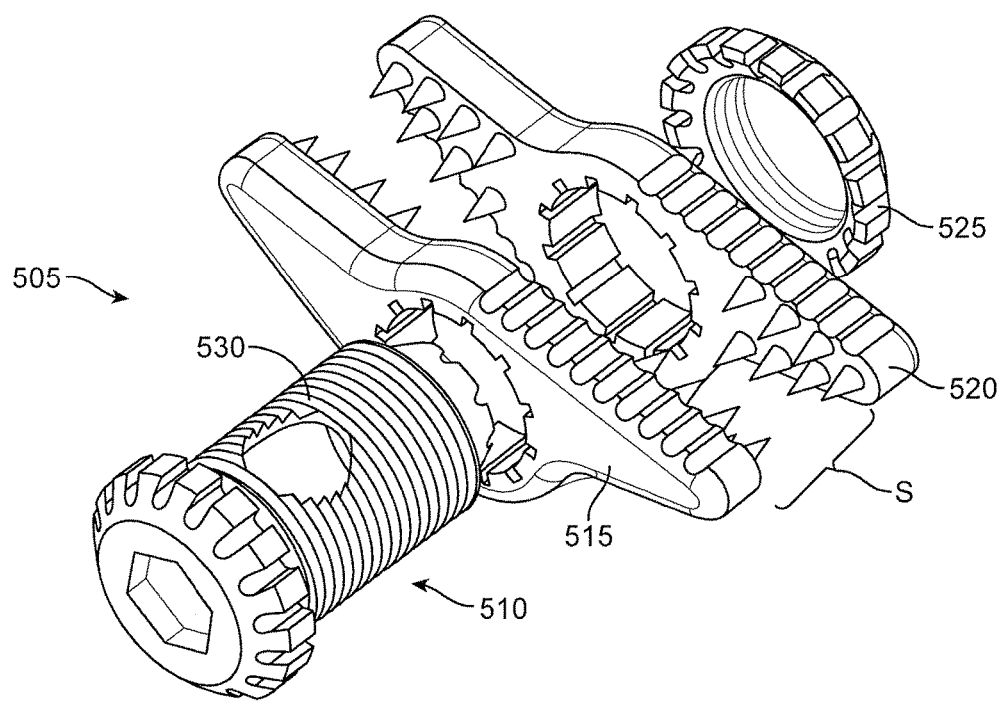
FIG. 5 shows another embodiment of an interspinous device.

FIG. 5 shows another embodiment of the ISP device, referred to as device 505. The device 505 includes four members including a first member 510, second member 515, third member 520, and fourth member 525. Each of the second, third, and fourth member has a central shaft or opening that is sized and shaped to receive an elongated shank 530 such that the members may be coupled to one another by inserting the shank 530 through the central openings of the other members. The fourth member 525 serves as a cap with internal threads that couple to external threads on the shank 530. In this manner, the fourth member 525 can be secured to the shank 530 with the second and third members 515 and 520 secured along the shank 530 between the fourth member 525 and an enlarged head 535 of the first member 510.

With reference still to FIG. 5, the second member 515 and third member 520 may be positioned with a space S therebetween. Each of the second member and third member are sized and shaped to be positioned adjacent or juxtaposed with a spinous process of a respective vertebra. The spinous process can be positioned within the space S and the second and third members tightened about the spinous process. The cap of the fourth member can then be tightened to secure the spinous process within the space S.

Figure 6:
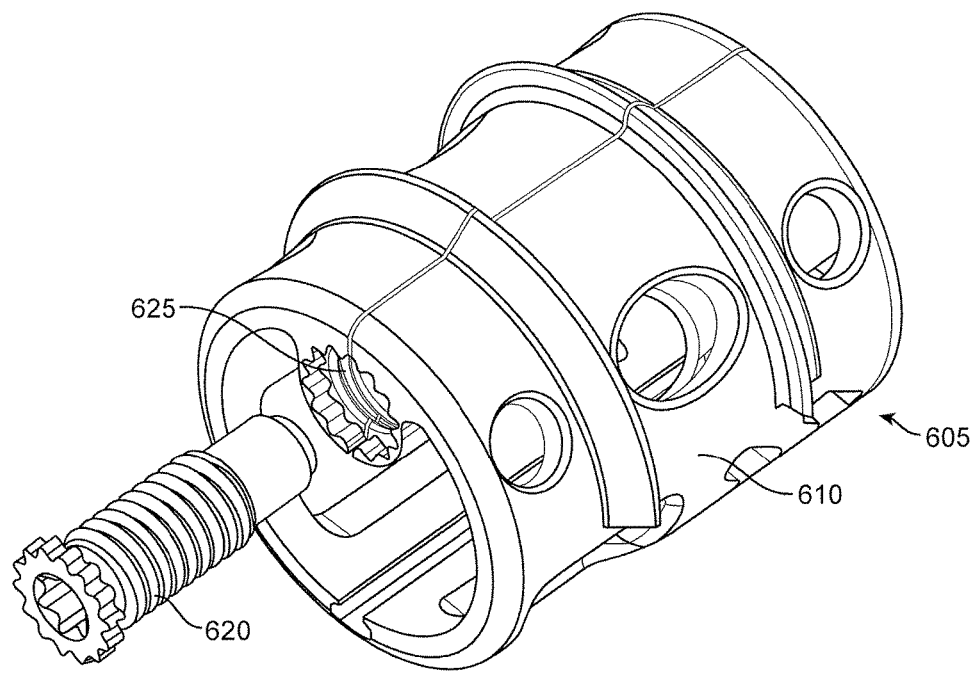

FIG. 6 shows another embodiment of the ISP device, referred to as device 605. The device 605 includes a main body 610 that is sized and shaped to be positioned within the space between a pair of spinous processes. The main body may be coupled to an expander member 615 that threadably inserts into an opening 625 in the main body 610.

The main body 610 has a substantially tubular configuration with an internal shaft and an out wall that forms a substantially cylindrical shape. A plurality of openings extend through the outer wall and communicate with the internal shaft.

The expander member 615 is elongated in shape and has a threaded shank that fits into the opening 625 of the main body. The expander member 615 can be rotated to engage with threads inside the opening 625 to engage the expander member 615 with the main body 610.

Any of the device embodiments can be made of any biologically adaptable or compatible materials such as Polyether ether ketone (PEEK). Additional materials considered acceptable for biological implantation are well known and include, but are not limited to, stainless steel, titanium, tantalum, combination metallic alloys, various plastics, resins, ceramics, biologically absorbable materials and the like. In addition, any of the devices may be packed with a bone graft or other suitable material for fusing to adjacent bone.

Figure 7:
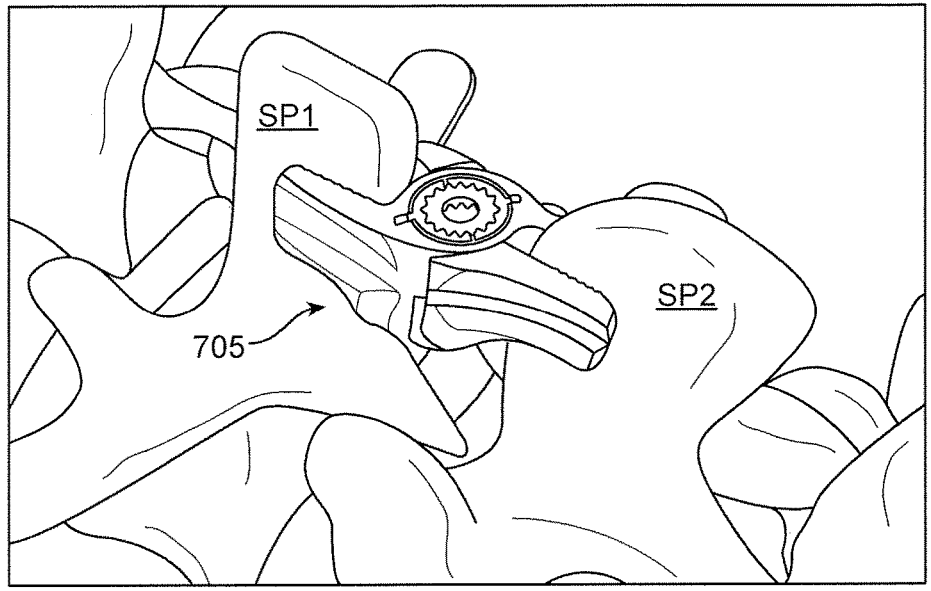
Figure 8:
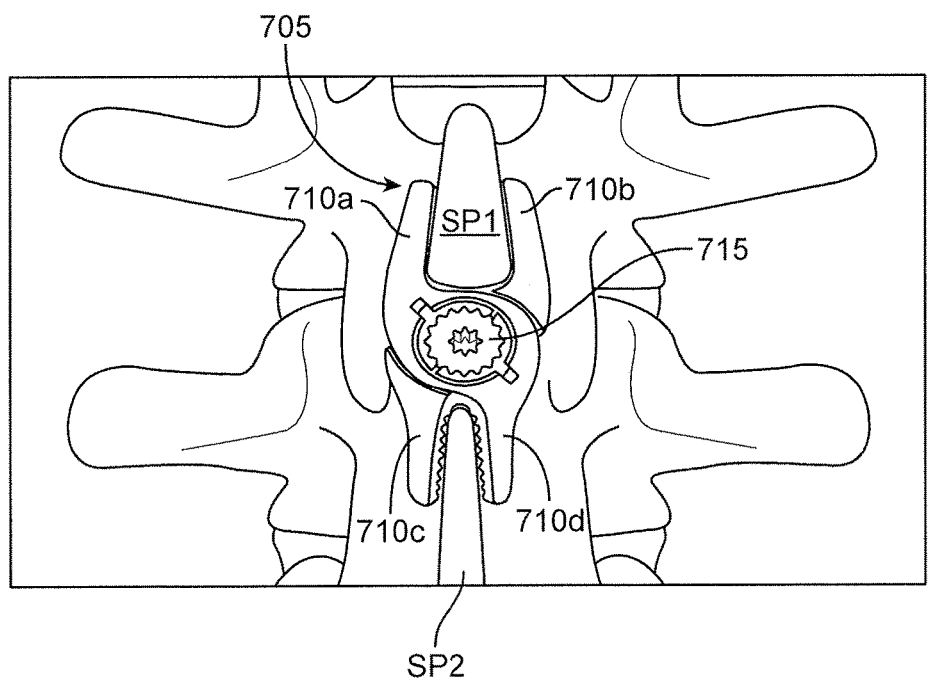

FIGS. 7 and 8 show another embodiment of a device 705 that is configured for placement between the spinous processes SP1 and SP2 of two adjacent vertebral bodies. The device 705 includes two pairs of arms including a first pair with first and second arms 710a and 710b, as well as a second pair with third and fourth arms 710c and 710d. The arms 710a and 710b in the first pair of arms are sized and shaped to grasp or otherwise couple to the spinous process SP1. Likewise, the arms 710c and 710d in the second pair of arms are sized and shaped to grasp or otherwise couple to the spinous process SP2. As described in detail below, the relative positions of the arms can be adjusted by rotating actuator 715.

Rotation of the actuator 715 causes the arms in a respective pair to rotate about an axis of rotation of the actuator 715. That is, the arms rotate about the axis in a scissor-like manner. This permits the arms to be opened up to a size that would accept a respective spinous process and then closed to a size that grasps the respective spinous process. In an embodiment, each arm has a flat inner surface with projections that are configured to increase a frictional hold with the spinous process to which the arm is coupled, as shown in FIGS. 9 and 10.

Figure 9:
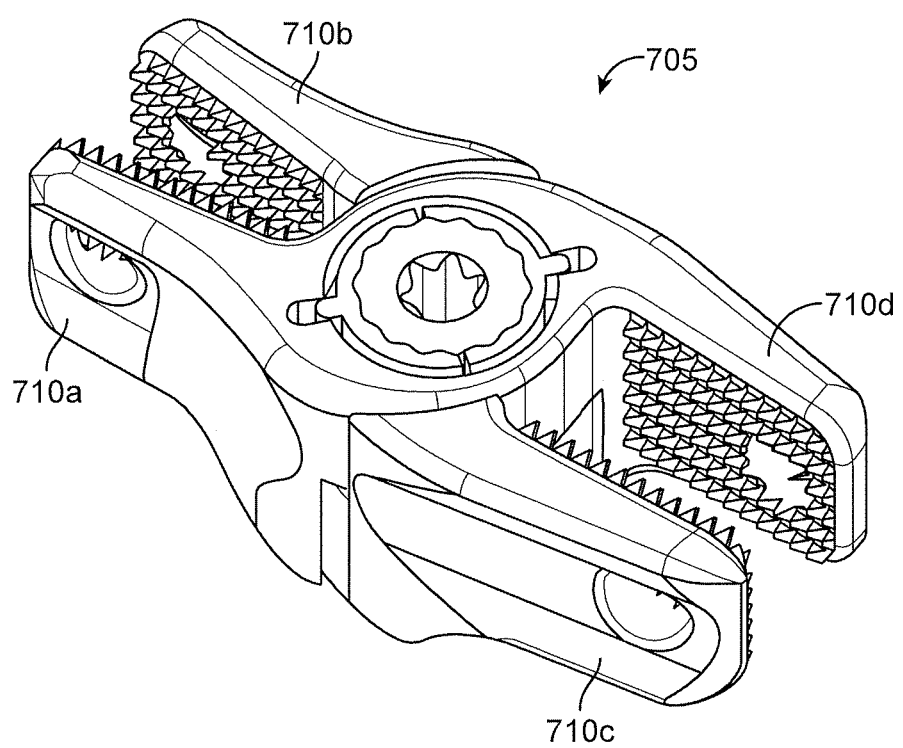
Figure 10A:
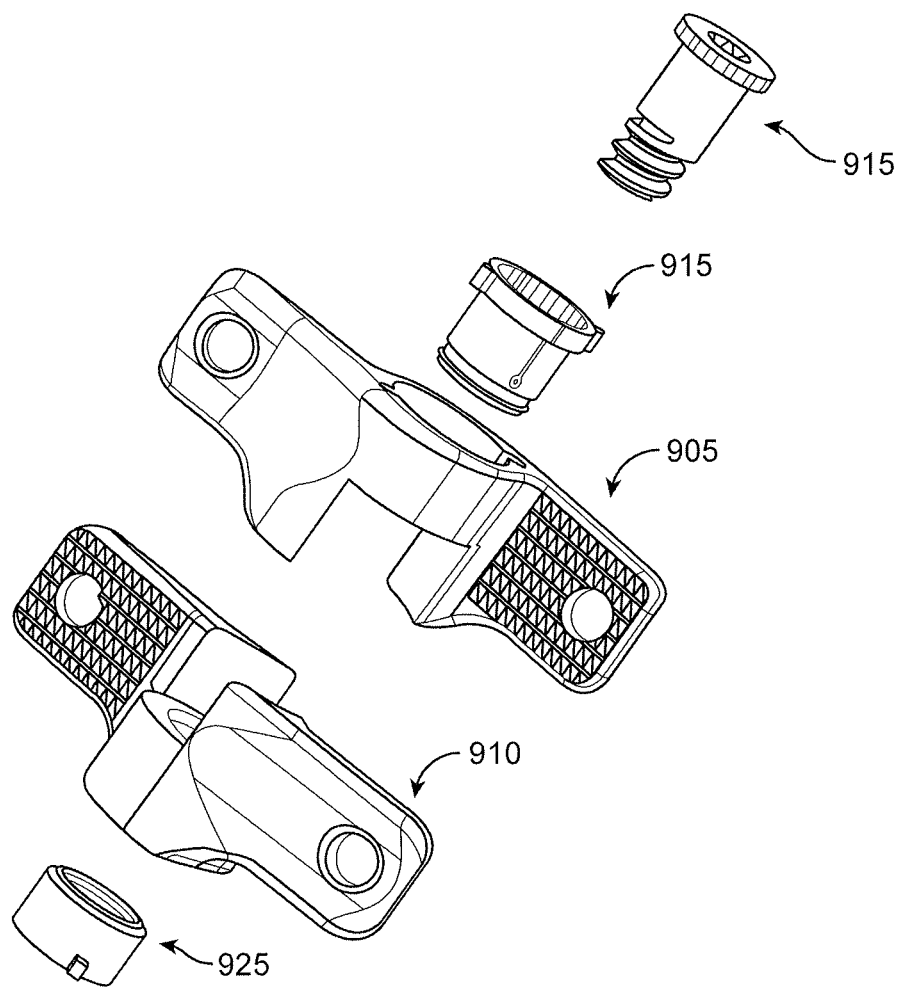

FIG. 9 shows a perspective view of the device 705 in an assembled state and FIG. 10A shows the device 705 in an exploded state. The device 705 includes a first arm member 905 that includes a pair of arms. A second arm member 910 includes another pair of arms. Each arm member includes a central shaft in which a coupler member 915 and a screw member 920 may be co-axially positioned. The screw member 920 couples to a cap 925 that is positioned on an opposite end of the screw member 920 to secure the device 705 in an assembled state. The coupler member 915 and screw member rotatably attach to the arm members 905 and 910. When the screw member is rotated, it causes the arm members 905 and 910 to also rotate such that the arms may be rotated toward and away from another.

Figure 10B:
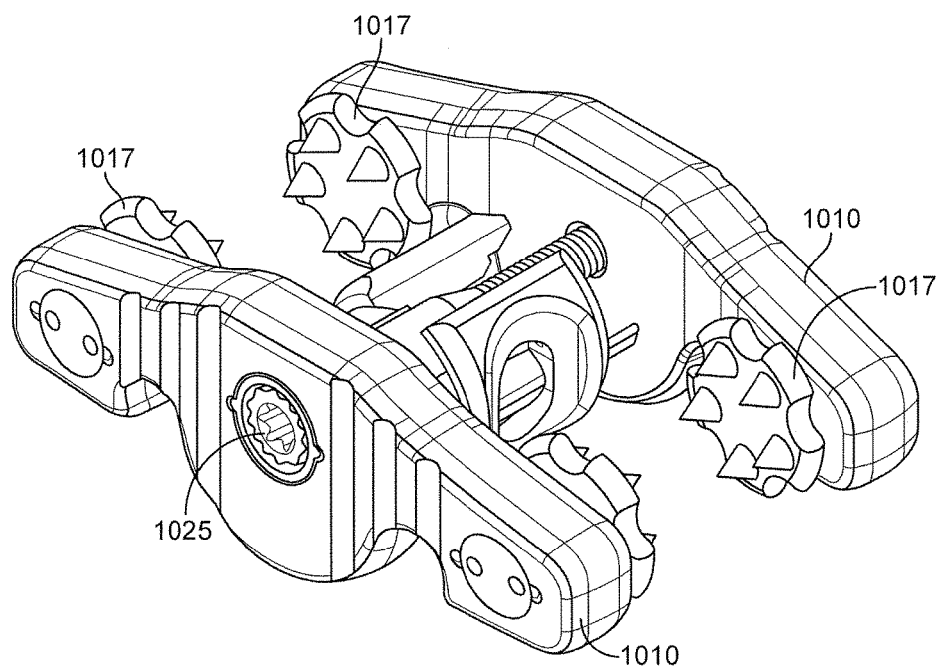
Figure 11:
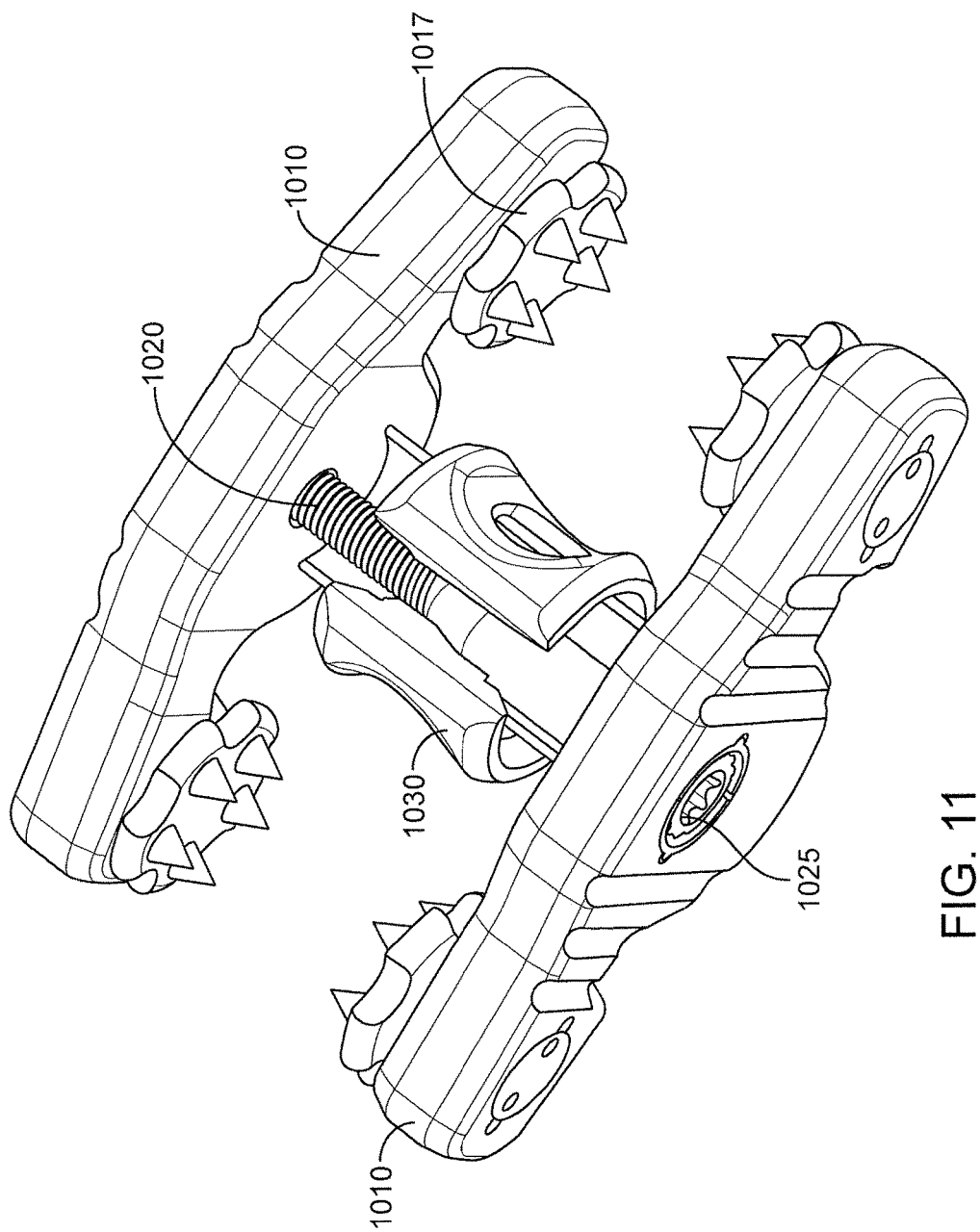

FIGS. 10B and 11 show another embodiment of the ISP device, referred to as device 1005. The device 505 includes a pair of opposed members 1010 that define a space S therebetween. Each of the members 1005 is sized and shaped to be positioned adjacent or juxtaposed with a spinous process of a respective vertebra. The spinous process can be positioned within the space S. In this regard, each of the members 1010 includes one or more pads 1017 having attachment elements, such as spikes, that are configured to attach onto the spinous process. The pads are attached to the members in a ball and socket manner such that the pads are configured to rotate and pivot about the ball and socket attachment.

With reference still to FIGS. 10B and 11, a connector 1020 connects the two members 1010 to one another. The connector 1010 is an elongated shaft having a first end with a head 1025 that sits in a seat in one of the members 1010. A second end region of the connector 1010 extends through a hole in the second member 1010. The connector 1020 and hole may be threaded such that rotation of the connector 1010 causes the two members 1010 to move toward or away from one another depending on the direction of rotation. In this manner, the spinous process may be secured between the two members 1010. An outer housing 1030 is positioned around the connector 1020. The outer housing is sized and shaped to receive bone material for fusing with the spine.

Figure 12:
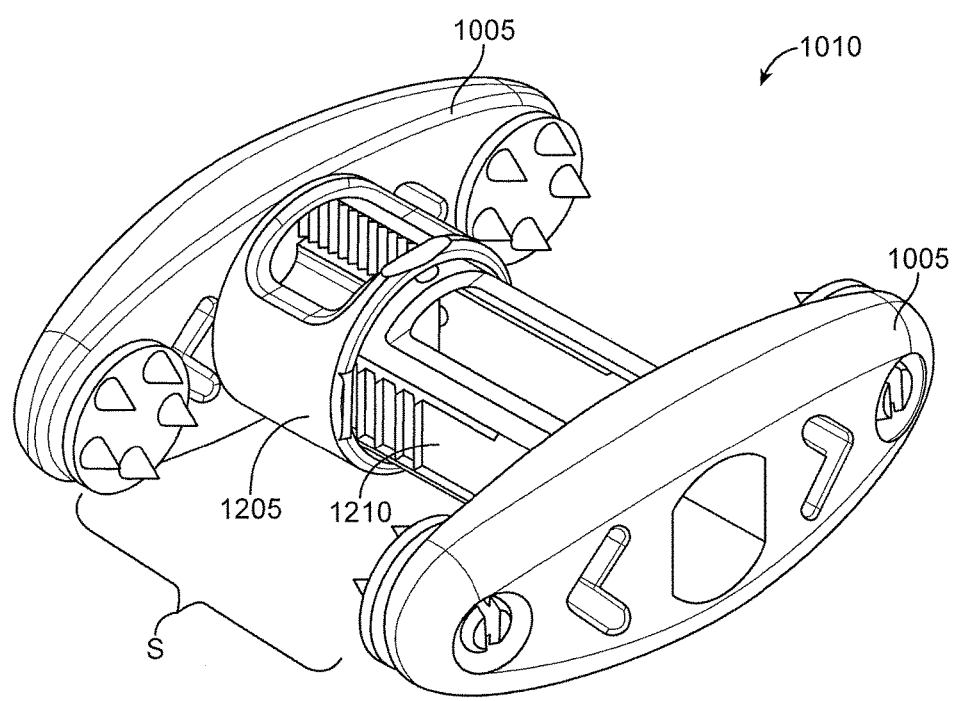
FIG. 12 shows another embodiment of an interspinous device.

In another embodiment, shown in FIG. 12, the device includes a pair of members 1005 and a connector 1010 therebetween. The connector is formed of a first connector member 1205 and a second connector member 1210 that coupled to one another such as in a male-female relationship. The connector members include a ratchet interface that permits the two connector members to be pushed toward one another in an interlocking fashion. The ratchet interface permits the two members 1005 to be successively moved toward one another and locked in successively closer positions so as to vary the size of the space S. The configuration of the ratchet can be varied to permit various increments of relative movement between the two members 1005.

Figure 13:
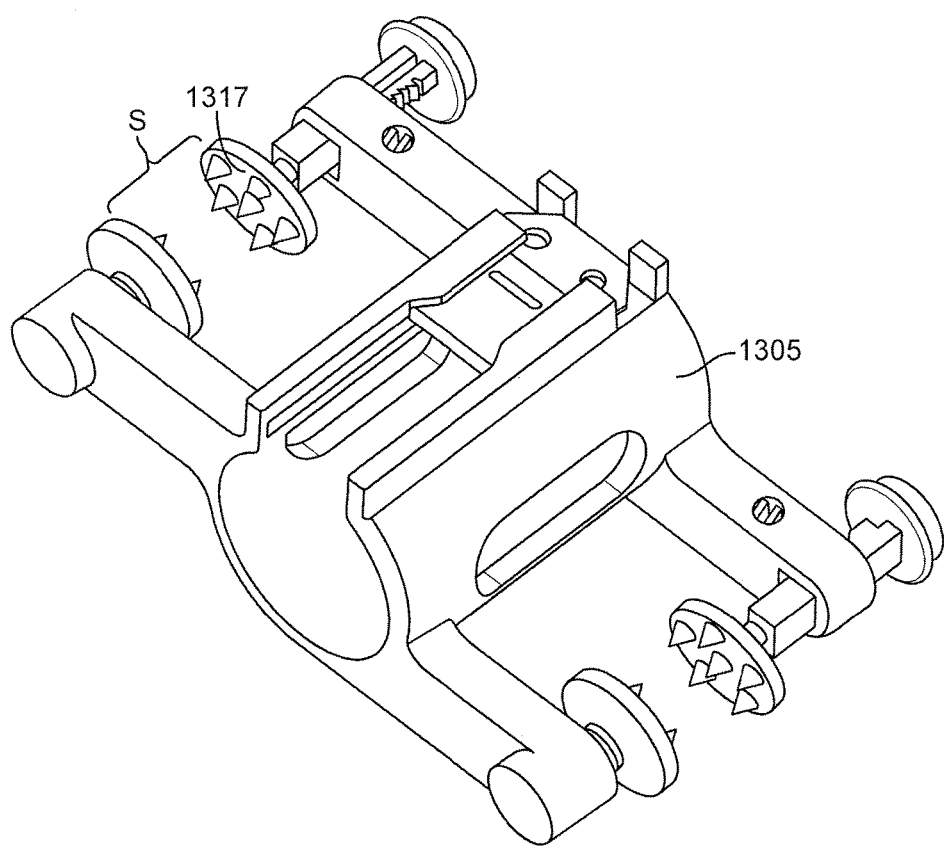
FIG. 13 shows another embodiment of an interspinous device.

In yet another embodiment, shown in FIG. 13, the device includes a pair of members 1005 that are monolithically coupled to one another via a connector 1305 that is monolithically attached to the two members. A set of pads 1317 are positioned on the members wherein the pads 1317 include attachment elements such as spikes. The pads 1317 define a space therebetween that is sized to receive an interspinous process. The positions of at least some of the pads can be moveably adjusted to vary the size of the space S between facing pads.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A spinal implant device, comprising:
    a first plate;
    a second plate positioned in an opposed position relative to the first plate;
    a first, at least partially cylindrical post extending outwardly from the first plate toward the second plate, the first post adapted to be positioned between first and second spinous processes of first and second vertebral bodies to limit movement of the first spinous process and the second spinous process toward one another, wherein the first post is a male member;
    a second, at least partially cylindrical post that mates with the first post, wherein the second post is a female member that receives the first post, the second post extending outwardly from the second plate toward the first plate;
    a ratchet interface that attaches the first post to the second post, wherein the ratchet interface permits the first and second posts to be pushed toward one another in an interlocking fashion such that the first and second posts can be successively moved toward one another and locked in successively closer positions without the aid of any other mechanical components;
    a first pad attached to the first plate, the first pad including a set of spikes adapted to engage a spinous process;
    a second pad attached to the second plate, the second pad including a set of spikes adapted to engage a spinous process; and
    wherein the first post has a pair of opposed, flat, external surfaces separated by a rounded external surface, and wherein the second post has a pair of opposed, flat, internal surfaces separated by a rounded internal surface, and wherein only the flat surfaces of the first and second posts are ratcheted and wherein the ratchets are separated by window openings in the rounded surfaces.

2. A device as in claim 1, wherein the first pad is configured to attach to an anterior segment of the spinous process.

3. A device as in claim 1, wherein the first pad is configured to attach to a laminal segment of the spinous process.

4. A device as in claim 1, wherein the second pad is configured to attach an anterior segment and a laminal segment of the spinous process.

5. A device as in claim 1, wherein the ratchet interface comprises a series of ratchets on one of the first post and the second post.

6. A device as in claim 1, wherein the set of spikes on the first pad is mounted on the first plate in a ball and socket configuration.

7. A device as in claim 1, wherein the first post is viewable through the window opening of the second post when positioned inside the second post.

\* \* \* \* \*